United States Patent
Kwon et al.

(10) Patent No.: US 10,568,940 B2
(45) Date of Patent: Feb. 25, 2020

(54) COMPOSITION FOR URIC ACID DECOMPOSITION USING GOLD NANOPARTICLES

(71) Applicant: GWANGJU INSTITUTE OF SCIENCE AND TECHNOLOGY, Gwangju (KR)

(72) Inventors: Inchan Kwon, Gwangju (KR); Secheon Jung, Incheon (KR)

(73) Assignee: GWANGJU INSTITUTE OF SCIENCE AND TECHNOLOGY, Gwangju (KR)

( * ) Notice: Subject to any disclaimer, the term of this patent is extended or adjusted under 35 U.S.C. 154(b) by 44 days.

(21) Appl. No.: 16/030,068

(22) Filed: Jul. 9, 2018

(65) Prior Publication Data

US 2019/0030136 A1 Jan. 31, 2019

(30) Foreign Application Priority Data

Jul. 25, 2017 (KR) .......................... 10-2017-0093873

(51) Int. Cl.
| | | |
|---|---|---|
| *A61K 38/44* | (2006.01) | |
| *A61P 7/00* | (2006.01) | |
| *A61K 9/51* | (2006.01) | |
| *A61K 33/24* | (2019.01) | |

(52) U.S. Cl.
CPC ............ *A61K 38/44* (2013.01); *A61K 9/5138* (2013.01); *A61K 33/24* (2013.01); *A61P 7/00* (2018.01); *C12Y 107/03003* (2013.01)

(58) Field of Classification Search
CPC ...... A61K 38/44; A61K 9/5138; A61K 33/24; A61K 9/00; A61K 47/02; A61K 38/443; C12Y 107/03003; A61P 7/00
See application file for complete search history.

(56) References Cited

FOREIGN PATENT DOCUMENTS

KR 101677945 B1 11/2016

OTHER PUBLICATIONS

Jung et al., "Synergistic Degradation of a Hyperuricemia-Causing Metabolite Using One-Pot Enzyme-Nanozyme Cascade Reactions," Mar. 13, 2017, pp. 1-8, Scientific Reports.
Nidhi Chauhan et al.. "An amperometric uric acid biosensor based on multiwalled carbon nanotube-gold nanoparticle moposite", Analytical Biochemistry, 413, 2011, p. 97-p. 103, Elsevier Inc.
Korean Office Action dated Sep. 27, 2018 for corresponding Korean Application No. 10-2017-0093873.

*Primary Examiner* — Robert S Cabral
(74) *Attorney, Agent, or Firm* — Hauptman Ham, LLP (57) ABSTRACT

A composition for uric acid decomposition using gold nanoparticles is disclosed.

The composition for uric acid decomposition in accordance with an exemplary embodiment of the present invention is characterized by including urate oxidase (UOX), gold nanoparticles and a buffer.

8 Claims, 6 Drawing Sheets

COMPOSITION FOR URIC ACID DECOMPOSITION USING GOLD NANOPARTICLES

CROSS-REFERENCE TO RELATED APPLICATION

This application claims priority to and the benefit of Korean Patent Application No. 10-2017-0093873, filed on Jul. 25, 2017, the disclosure of which is incorporated herein by reference in its entirety.

BACKGROUND

1. Field of the Invention

The present invention relates to a composition for uric acid decomposition to improve a decomposition efficiency of uric acid, and more particularly to a composition for uric acid decomposition using gold nanoparticles.

2. Description of Related Art

Hyperuricemia refers to a state of abnormally high concentration of uric acid in the blood and is known to be associated with diseases such as cardiovascular disease, kidney diseases, gout, and tumor lysis syndrome (TLS).

Urate oxidase (UOX) is an enzyme that decomposes uric acid into 5-hydroxyisourate and hydrogen peroxide ($H_2O_2$), and is used to treat hyperuricemia. Rasburicase and pegloticase manufactured by recombining urate oxidase are used as a therapeutic agent for diseases related to hyperuricemia.

Urate oxidase (UOX) generates hydrogen peroxide in a process of decomposing uric acid. Hydrogen peroxide is a kind of active oxygen, and causes various side effects as follows.

First, when urate oxidase is administered to a patient deficient with G6PD (glucose-6-phosphate dehydrogenase) enzyme, it reacts sensitively to hydrogen peroxide produced by uric acid decomposition and causes methemoglobinemia. The G6PD enzyme plays a role in removing the active oxygen generated in a human body. A deficiency of G6PD enzyme is the most common enzyme deficiency disorder in humans, which reduces or destroys an oxygen transport capacity of hemoglobin when the human body is in an oxidative stress state.

Therefore, the administration of Urate oxidase is limited for G6PD deficient patients.

Second, hydrogen peroxide is decomposed by the fenton reaction to produce a hydroxy radical, which is one of the strong reactive oxygen species. Hydroxy radicals have been reported to cause a genetic modification.

Thirdly, the reaction product, hydrogen peroxide, interferes with an enzyme activity of the urea oxidase, thereby reducing an uricolytic activity of the urea oxidase.

In order to solve this side effect, the studies using catalase, which is an enzyme of decomposing hydrogen peroxide, have been proceeded. However, since catalase has low stability, it has a problem of easily losing an activity of decomposing hydrogen peroxide.

A background art related to the present invention is Korean Patent Registration No. 10-1677945 (registered on Nov. 15, 2016), which discloses a method for reducing compounds and uric acid.

SUMMARY OF THE INVENTION

It is an object of the present invention to provide a composition for uric acid decomposition by removing hydrogen peroxide generated by uric acid decomposition, by using gold nanoparticles (AuNP nanozyme) having the enzyme activity for decomposing hydrogen peroxide.

The composition for uric acid decomposition in accordance with an exemplary embodiment of the present invention in order to accomplish the one object is characterized by including urate oxidase (UOX), gold particles, and a buffer.

The gold nanoparticles may have a polymer coating layer formed on its surface, and the polymer may include at least one of polyvinylpyrrolidone (PVP) and polyethylene glycol (PEG).

Gold nanoparticles may have an average particle diameter of 5 to 20 nm.

The composition for degrading uric acid may contain 0.5 to 5 μg/mL of gold nanoparticles.

The concentration of the uricolytic enzyme may be 1 to 20 nM.

The buffer may include a phosphate buffered saline (PBS), a tris buffer, a carbonate buffer, a borate buffer, or a phosphate buffer.

The pH of the buffer may be 8.0 to 9.5.

The concentration of the buffer may be 5 to 30 mM.

In accordance with an exemplary embodiment of the present invention, it is possible to remove hydrogen peroxide generated upon decomposition of uric acid by using gold nanoparticles having the enzymatic activity for decomposing hydrogen peroxide, and by using gold nanoparticles and uric acid decomposing enzyme together, it is possible to reduce the decomposition time of uric acid by about 5 times or more than when using urate oxidase only, In the present invention, by using the composition for uric acid decomposition including polymer-coated gold nanoparticles, it is possible to reduce side effects generated by administration of urate oxidase and reduce the number of administrating urate oxidase since an effect of urate oxidase is increased, thereby increase an inconvenience of the patient. In addition, through the hydrogen peroxide decomposition activity of gold nanoparticles, applications for treating various diseases such as hyperuricemia are possible.

BRIEF DESCRIPTION OF THE DRAWINGS

FIGS. 3A, 3B, and 3D are graphs

DETAILED DESCRIPTION OF EXEMPLARY EMBODIMENTS

The advantages, the features of the present invention and the method of achieving them will become apparent with reference to the embodiments described in detail below together with the accompanying drawings. However, the present invention may be embodied in many different forms and is not limited to the embodiments disclosed below. Rather, the present embodiments are provided so that the disclosure of the present invention will be complete, and will fully convey the scope of the invention to those skilled in the art to which the present invention pertains. The present invention is merely defined by the scope of claims. Like reference numerals refer to like elements throughout the specification.

Hereinafter, the uric acid decomposition using gold nanoparticles according to a preferred embodiment of the present invention will be described in detail with reference to the accompanying drawings.

Urate oxidase (UOX) decomposes uric acid, which causes hyperuricemia, but it causes various health problems because it produces hydrogen peroxide ($H_2O_2$) upon decomposition of uric acid.

In the present invention, it is to provide a method capable of decomposing uric acid about 5 times faster than when using urate oxidase (UOX) alone, by removing hydrogen peroxide having cytotoxicity using gold nanoparticles formed with a polymer coating layer.

Figure 1:
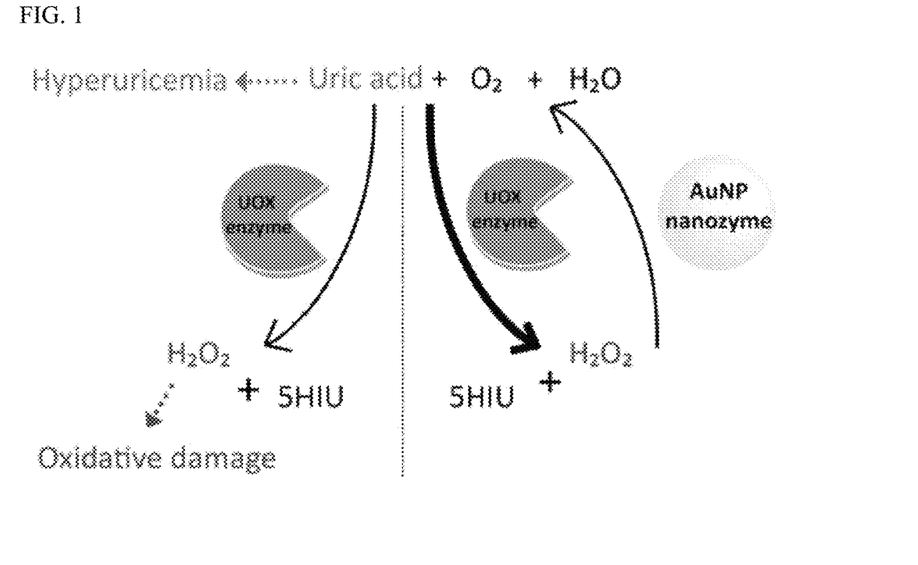
FIG. 1 is a mechanism showing an uric acid decomposition process in accordance with an exemplary embodiment of the present invention.

FIG. 1 is a mechanism showing the uric acid decomposition process in accordance with an exemplary embodiment of the present invention. Uric acid is decomposed into 5-hydroxyisourate and hydrogen peroxide ($H_2O_2$) by UOX enzyme in the presence of oxygen and water (left side of FIG. 1). The hydrogen peroxide ($H_2O_2$) can be dissociated into water and oxygen by gold nanoparticles (AuNP nanozyme). When uric acid is decomposed using both urate oxidase and gold nanoparticles, the uric acid decomposition rate is increased (right side of FIG. 1).

In the present invention, by removing the hydrogen peroxide having a cytotoxicity using gold nanoparticles (AuNP nanozyme), it is possible to reduce the decomposition time of uric acid about 5 times or more than when using UOX enzyme alone. In other words, UOX enzyme and gold nanoparticles (AuNP nanozyme) can be used together to remove the hydrogen peroxide generated upon decomposition and improve the efficacy of uric acid decomposition simultaneously.

The composition for uric acid decomposition in accordance with an exemplary embodiment of the present invention is characterized by including urate oxidase (UOX), gold nanoparticles and a buffer.

More specifically, the composition for uric acid decomposition may include 1 to 20 nM of urate oxidase, 0.5 to 5 μg/mL of gold nanoparticles, and 5 to 30 mM of buffer. The composition for uric acid decomposition of satisfying this range exhibits an excellent uric acid decomposition efficacy of urate oxidase when uric acid concentration is 50 to 200 μM.

In the present invention, the uric acid decomposition efficacy of urate oxidase can be improved, by using a composition including urate oxidase (UOX), gold nanoparticles, and a buffer.

In order to prevent the nanoparticles from aggregating each other, a coating material is formed on its surface. When there is no coating material on the surface of the nanoparticles, the nanoparticles will aggregate together, and as the size increases, it becomes difficult to maintain the nano-size.

Therefore, it is preferable that gold nanoparticles have a polymer coating layer formed on the surface thereof. Considering that gold nanoparticles have an excellent biocompatibility, the gold nanoparticles coated with the polymer are harmless to the human body, and it will show a negligible toxicity. The polymer includes at least one of polyvinylpyrrolidone (PVP) and polyethylene glycol (PEG), and polyvinylpyrrolidone and polyethylene glycol are also used as plasma substitutes.

Since the surface area to volume ratio becomes larger as the average particle diameter of gold nanoparticles is smaller. Thus, the smaller the average particle diameter of gold nanoparticles, the more efficient the catalytic action. Accordingly, it is preferable that the average particle diameter of gold nanoparticles is 5 to 20 nm, and when it is outside this range, the activity of the urate oxidase (UOX) decreases.

As the content of gold nanoparticles increases, the rate of urate oxidase increases as the activity of urate oxidase increases. In step (a), it is preferable that it includes gold nanoparticles 0.5 to 5 μg/mL. When it is outside of the range, it shows a decomposition rate similar to when using urate oxidase (UOX) alone, without an improvement of the uric acid decomposition efficacy.

The buffer may include, for example, a phosphate buffered saline (PBS), a tris buffer, a carbonate buffer, a borate buffer, or a phosphate buffer, as a liquid buffer.

When the buffer satisfies pH 8.0 to 9.5, the decomposition of hydrogen peroxide and the decomposition rate of uric acid are excellent. As the pH increases from 8.0 to 9.5, the amount of dissociated hydrogen peroxide increases by about 12 times or more, and the decomposition rate of uric acid also increases by about 40% or more than when using urate oxidase (UOX) alone.

The concentration of the buffer may be 5 to 30 mM, for example, the concentration of the borate buffer may be 20 mM.

The composition for uric acid decomposition by using gold nanoparticles in accordance with an exemplary embodiment of the present invention is prepared by mixing urate oxidase (UOX), gold nanoparticles, and a buffer. The matters with regard to gold nanoparticles and the like are as described above.

The composition for uric acid decomposition by using gold nanoparticles in accordance with an exemplary embodiment of the present invention will be described in detail with reference to FIGS. 2 to 6.

First, gold nanoparticles coated with PVP (5 nm, 10 nm, and 20 nm), PEG (5 nm), CA (citric acid, 5 nm), or TA (tannic acid, 5 nm) were purchased from nanoComposix Inc. (San Diego, Calif.). The numerical values in the above parenthesis mean the average particle diameter of gold nanoparticles. Ni-nitrilotriacetic acid (Ni-NTR) agarose and pQE80 plasmid were purchased from Qiagen (Valencia, Calif.).

A Vivaspin centrifugal concentrator with a molecular weight cut-off (MWCO) of 50 kDa was purchased from Sartorius Corporation (Bohemia, N.Y.). A PD-10 desalting column was obtained from GE Health Care (Piscataway, N.J.) and all other chemicals were purchased from Sigma-Aldrich Corporation (St. Louis, Mo.).

An expression vector of recombinant urate oxidase (UOX), such as rasburicase, was derived from *Aspergillus flavus* with a hexa histidine tag, pQE80-UOX. The pQE80-UOX plasmid was transformed into TOP10 *E. coli* cells for the expression of UOX to obtain TOP10 [UOX] cells. The preincubated TOP10 [UOX] cells were inoculated into a newly prepared 2×YT medium containing 100 µg/ml ampicillin. Cells were then shaken (220 rpm) at 37° C. until an optical density (OD) at 600 nm reaches 0.5. 1 mM IPTG was added to the cultured TOP10 [UOX] cells to induce a protein expression. After an induction for 5 hours, the cells were pelleted by centrifugation at 12,000 rpm for 30 minutes. The cell pellet was then resuspended in lysis buffer (pH 7.5) containing 50 mM sodium phosphate, 0.3 M NaCl, and 10 mM imidazole to purify UOX. Cell pellets resuspended in the lysis buffer were incubated with lysozyme (200 µg/ml) for 30 minutes on ice. The lysozyme-cultured cell pellet was sonicated on ice for 10 minutes (10 seconds pulse on and 20 seconds pulse off). The lysis of the cell was pelleted by centrifugation at 12,000 rpm, 4° C. for 30 minutes, and a supernatant was transferred to a new tube. Ni-NTA agarose was mixed with the supernatant for 1 hour while shaking it at 220 rpm. The supernatant mixed with Ni-NTA agarose was loaded onto the column, and washed with a wash buffer (pH 7.5) containing 50 mM sodium phosphate, 0.3 M NaCl and 20 mM imidazole. Elution of the proteins was performed by elution buffer (pH 7.5) containing 50 mM sodium phosphate, 0.3 M NaCl, and 250 mM imidazole. Using the PD-10 column, the protein solution buffer was replaced with PBS buffer (pH 7.4).

The molar absorption coefficient of UOX at 280 nm was reported to be 53,400 $M^{-1}$ $cm^{-1}$. The protein concentration was determined according to Beer-Lambert law (Biotek, Winooski, Vt.) by measuring a molar absorbance at 280 nm using a Synergy H1 four multimode microplate reader (BioTek).

A kinetic analysis of UOX was performed by the spectrophotometric method. A reaction in which uric acid is oxidized into 5-hydroxyisourate (SHIU) is determined by monitoring the absorbance reduction at 293 nm at 25° C. in a standard 96-well plate of four multimode microplate reader (BioTek, Winooski, Vt.).

The decomposition rate (µM/min) of uric acid was obtained by dividing the molar absorption rate (12,300$M^{-1}$ $cm^{-1}$) of uric acid by the OD change rate ($min^{-1}$). A kinetic parameter of UOX at 5 nM were measured in 20 mM borate buffer (pH 9.5) at various uric acid concentrations. To obtain $V_{max}$, $K_m$, and $k_{cat}$, the Michaelis-Menten model was applied to the average consumption rate of each uric acid concentration.

TEM (JEOL, JEM-2100, Peabody, Mass.) was used for the morphological and size analysis of 5 nm gold nanoparticles coated with PVP (Au@PVP). A drop of Au@PVP was applied to a 200-mesh carbon-coated copper grids and dried in vacuum oven at 25° C. The TEM images of Au@PVPs were analyzed using ImageJ software to determine the particles size-distribution.

The catalytic activity of gold nanoparticles (AuNP) was measured with a spectrophotometer, and the decrease in absorbance at 240 nm caused by a degradation of hydrogen peroxide was measured in triplicates at 25° C. by Synergy H1 four multimode microplate reader. Prior to every measurement, the plates were shaken for 30 seconds to remove oxygen bubbles generated upon hydrogen peroxide degradation. The absorbance of hydrogen peroxide during the reaction was used as a blank.

Figure 2A:
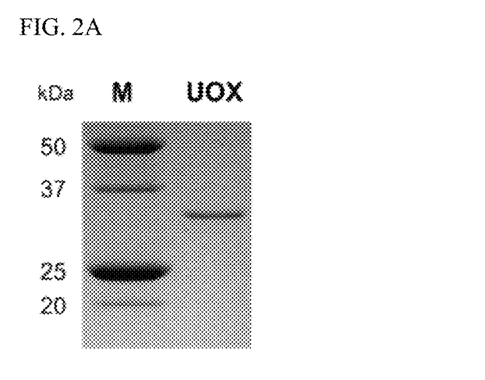
FIG. 2A is a photograph and FIGS. 2B, 2C, and 2D are graphs showing a property of UOX enzyme.
Figure 2B:
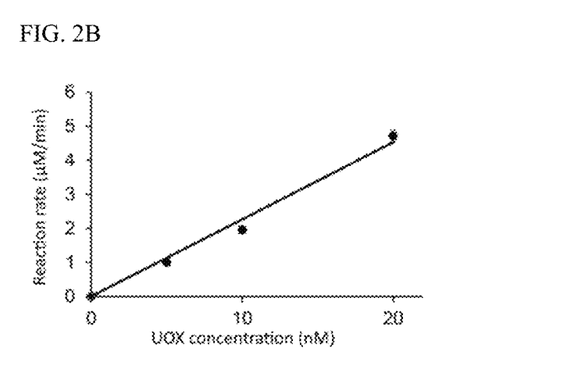
Figure 2C:
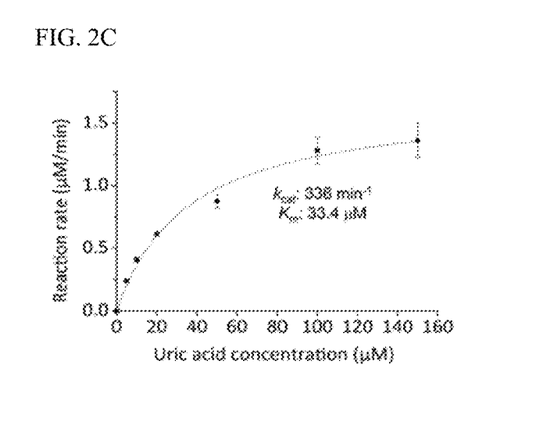
Figure 2D:
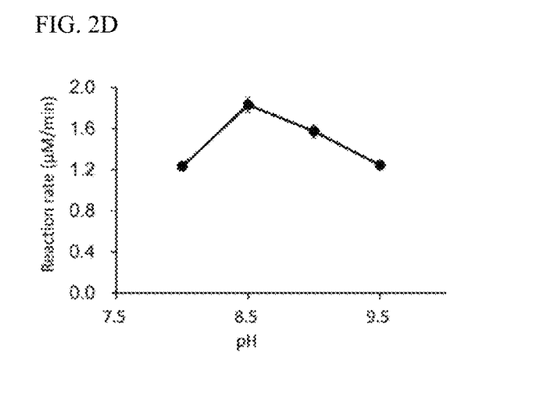

FIG. 2A is a photograph and FIGS. 2B, 2C, and 2D are graphs showing a property of UOX enzyme. FIG. (A) SDS-PAGE gel image of UOX enzyme, M and UOX denote the lanes for molecular weight markers and purified UOX. (B) A graph showing the reaction rate of uric acid decomposition at a concentration of 0-20 nM of UOX enzyme. UOX was reacted with 100 µM uric acid dissolved in 20 mM borate buffer (pH 9.5). (C) A graph showing by applying UOX to the Michaelis-Menten formula, and all reactions were performed in 20 mM borate buffer (pH 9.5) containing 5 nM UOX. (D) A graph showing an activity tendency of UOX depending on pH, and 100 µM uric acid was converted by 5 nM UOX contained in 20 mM borate buffer in the pH range of 8.0 to 9.5.

Referring to FIG. 2(A), the single band was located between a molecular weight of 25-37 kDa, which is coincident with an expected molecular weight of UOX of 33.4 kDa.

Referring to FIG. 2(B), the initial decomposition rate of uric acid by UOX was obtained by monitoring the absorbance at 293 nm, by using 20 mM borate buffer (pH 9.5) containing 0 to 20 nM UOX. When 100 µM uric acid is present, the initial reaction rate of uric acid decomposition by UOX shows a linear increase as the concentration of UOX increases up to 20 nM.

Referring to FIG. 2(C), the initial uric acid decomposition rate by 5 nM UOX at a concentration of 0 to 150 µM uric acid was about three times or more in 20 mM borate buffer (pH 9.5).

Referring to FIG. 2(D), the catalytic activity of UOX was measured in the presence of 5 nM UOX and 100 uM uric acid were present at a pH range of 8.0 to 9.5, and a maximum catalytic activity of UOX was observed at pH 8.5. These results show that the purified UOX efficiently decomposes uric acid.

The term "Au@PVP" in the drawings which will be described below refers to gold nanoparticles coated with PVP and having an average particle diameter of 5 nm.

Figure 3A:
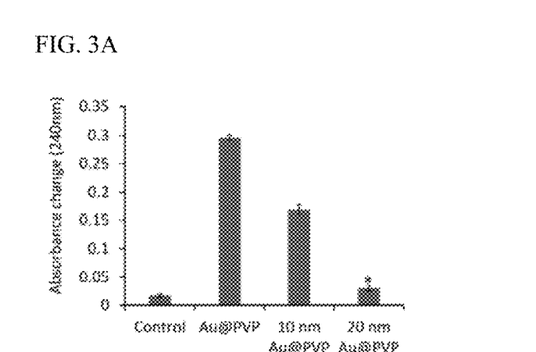
Figure 3B:
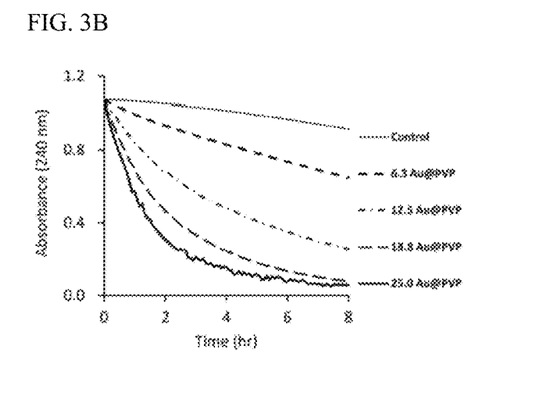
Figure 3C:
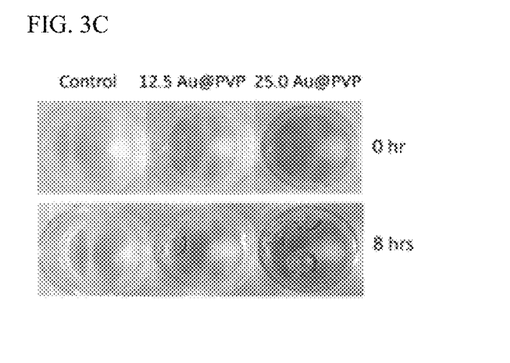
FIG. 3C is a photograph showing a property of gold nanoparticles (Au@PVP) coated with polyvinylpyrrolidone.
Figure 3D:
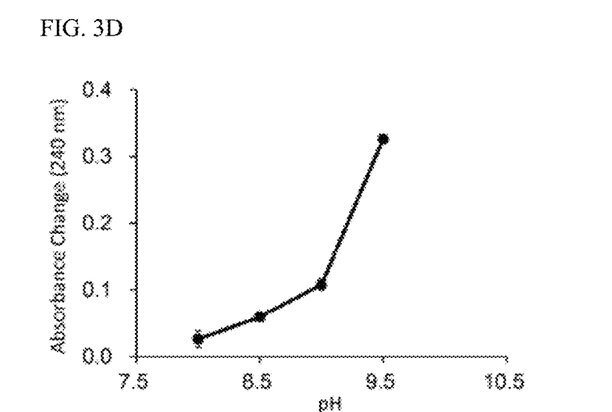

FIGS. 3A, 3B, and 3D are graphs and FIG. 3C is a photograph showing a property of gold nanoparticles (Au@PVP) coated with polyvinylpyrrolidone. (A) A graph showing the decomposition activity of hydrogen peroxide according to Au@PVP (12.5 µg/mL) having different average particle diameters. The absorbance was measured at 240 nm for 3 hours in a 20 mM borate buffer (pH 9.5) to confirm the composition activity of 25 mM of hydrogen peroxide. (B) A graph showing the dissociation time of hydrogen peroxide according to the content of Au@PVP. (C) A photograph of the oxygen bubbles generated when Au@PVP decomposes hydrogen peroxide into water and oxygen. (D) A graph showing the decomposition of hydrogen peroxide according to Au@PVP in the pH range of 8.0 to 9.5 for 3 hours.

Referring to FIG. 3(A), it can be confirmed while a control having hydrogen peroxide, without UOX enzyme, and gold particles has a very low uric acid decomposition activity, as the average particle diameter of Au@PVP is smaller, the enzyme decomposition activity of Au@PVP is increased. This is because the smaller the average particle diameter of the gold nanoparticles, the larger the surface area to volume ratio, and thus the catalytic action is more efficient.

Referring to FIG. 3(B), to measure the dissociation time of hydrogen peroxide according to Au@PVP with contents of 0, 6.3, 12.5, 18.8 and 25.0 µg/mL, the 96-well plate having the sample was shaken for 30 seconds. The decomposition of hydrogen peroxide was measured by a change in absorbance at 240 nm. Hydrogen peroxide was decomposed itself under basic conditions, but it was very slow compared to UOX+Au@PVP. In addition, the time course curve of the hydrogen peroxide dissociation in the presence of 25.0 µg/mL Au@PVP shows a slight variation due to some oxygen bubbles generated by too rapid decomposition of hydrogen peroxide.

Referring to FIG. 3(C), oxygen bubbles were generated as hydrogen peroxide is dissociated into oxygen and water in an aqueous solution, and no oxygen bubbles were observed in the absence of Au@PVP. However, in the presence of 12.5 µg/mL Au@PVP, oxygen bubble formation was clearly observed after 8 hours. Also, as the amount of Au@PVP was increased to 25.0 µg/mL, more oxygen bubble formation was observed. However, Au@PVP less than 25.0 µg/mL, such as the change in absorbance time change, was not observed for Au@PVP, and it is expected that oxygen bubbles are removed by shaking.

Referring to FIG. 3(D), as the pH increases from 8.0 to 9.5, it shows a result that the amount of dissociated hydrogen peroxide increases by about 12 times or more.

Figure 4:
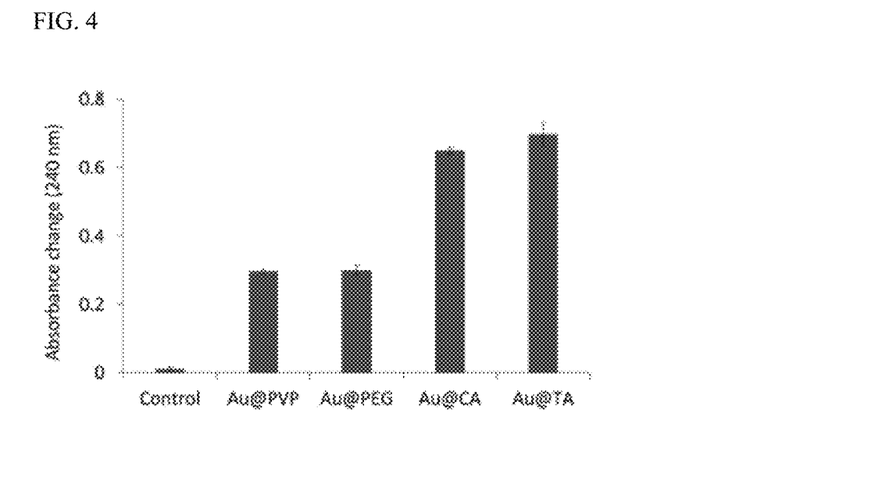
FIG. 4 is a graph comparing the catalytic activities of gold nanoparticles (25.0 μg/mL) coated with PVP, PEG, CA, and TA, respectively.

FIG. 4 is a graph comparing the catalytic activities of gold nanoparticles (25.0 µg/mL) coated with PVP, PEG, CA, and TA, respectively. Hydrogen peroxide decomposition by coated gold nanoparticles (25.0 µg/mL) was observed in 20 mM borate buffer (pH 9.5) for 3 hours.

It shows a result that the amount of hydrogen peroxide decomposed by Au@CA and Au@TA is about twice as large as the amount of hydrogen peroxide decomposed by Au@PVP and Au@PEG. From this, it can be seen that the scavenging activity of hydrogen peroxide/hydroxyl radical of TA and CA is attributed to an enhancement of hydrogen peroxide decomposition activities of Au@CA and Au@TA.

Based on the catalytic activities of UOX and gold nanoparticles, a UOX-AuNP nanozyme cascade reaction was performed to decompose uric acid. In this reaction, UOX converts uric acid to 5-hydroxyisourate and hydrogen peroxide ($H_2O_2$), and then dissociates hydrogen peroxide into oxygen and water by gold nanoparticles (AuNP nanozyme).

Therefore, as the intermediate hydrogen peroxide is continuously removed by gold nanoparticles, decomposition of uric acid by UOX is promoted.

In the absence and presence of gold nanoparticles, uric acid decomposition by 5 mM UOX was performed in 20 mM borate buffer (pH 9.5). Uric acid decomposition was observed by measuring the absorbance at 293 nm.

FIGS. 5A, 5B, 5C, and 5D are graphs showing the results of the cascade reaction by using UOX alone and UOX+Au@PVP. (A) is a graph showing the decomposition rate of uric acid of 5 mM UOX by using Au@PVPs (5.0 µg/mL) having an average particle diameter of 5, 10 and 20 nm, and the rate measurement is performed in 20 mM borate buffer (pH 9.5) containing 100 µM uric acid. (B) 100 µM uric acid decomposition rate when 5 mM UOX alone and 5 mM UOX+0.5, 1.3, and 5.0 µg/mL Au@PVP in 20 mM borate buffer (pH 9.5) (C) 100 µM uric acid decomposition time when 5 mM UOX alone and 5 mM UOX+0.5, 1.3, 5.0 µg/mL Au@PVP in 20 mM borate buffer (pH 9.5) (D) 100 µM uric acid decomposition rate when 5 mM UOX alone and 5 mM UOX+5.0 µg/mL Au@PVP in the pH range of 8.0 to 9.5.

Figure 5A:
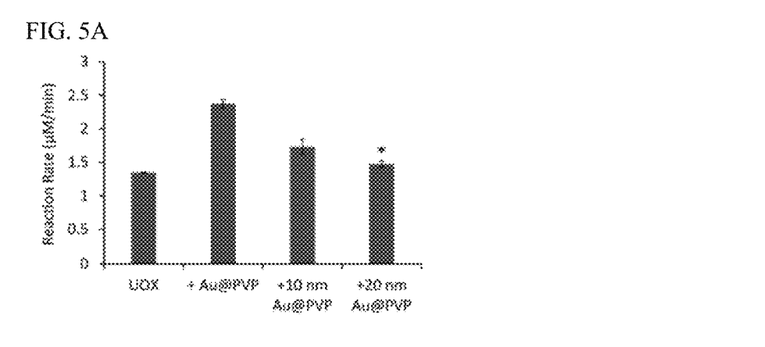
FIGS. 5A, 5B, 5C, and 5D are graphs showing the results of the cascade reaction using UOX alone, and UOX+Au@PVP.

Referring to FIG. 5(A), as the average particle diameter of the PVP-coated gold nanoparticles (Au@PVP) increases, the decomposition rate of uric acid using UOX and AuNPs decreases. As described in FIG. 3(A), as the average particle diameter of the nanoparticles is smaller, it means that the surface area of the nanoparticles is increased and an ability to decompose hydrogen peroxide is increased, and the catalytic action is efficient. Due to the above, when using polymer-coated gold nanoparticles with UOX, the smaller the size of gold nanoparticles, the greater the activity of UOX.

Figure 5B:
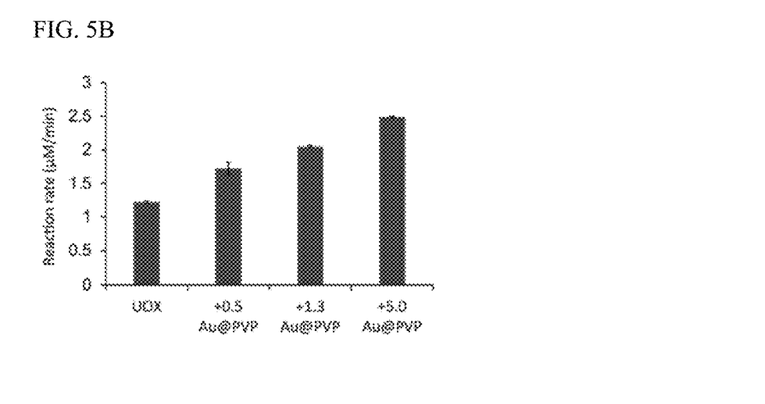

Referring to FIG. 5(B), it can confirm that as the content of Au@PVP increases, the decomposition rate of uric acid increases and the decomposition time of uric acid decreases. The decomposition rate of uric acid at 5.0 µg/mL Au@PVP shows the speed about twice or more faster than compared to the decomposition rate of uric acid in the absence of Au@PVP.

Figure 5C:
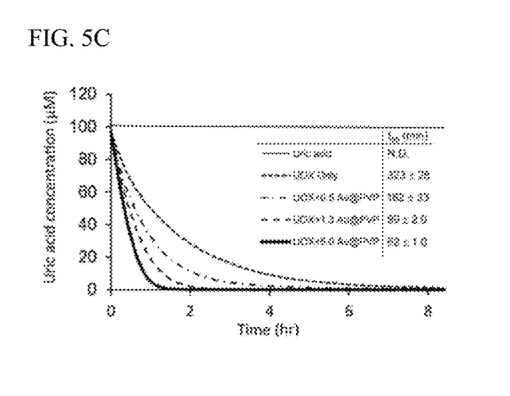

Referring to FIG. 5(C), when no Au@PVP was present, the time required for 95% uric acid decomposition (t95) was 323 minutes, and as expected, in the presence of 0.5, 1.3, 5.0 g/mL Au@PVP, the time required for 95% uric acid decomposition (t95) decreased to 182, 99, and 62 mins, respectively. That is, in the presence of 5.0 µg/mL Au@PVP and UOX, the 95% uric acid decomposition (t95) time was reduced more than 5 times than in the presence of UOX alone.

Therefore, in the presence of the polymer-coated gold nanoparticles and urate oxidase, the acceleration of the decomposition rate of uric acid results from hydrogen peroxide decomposed into oxygen and water, and a supplement of oxygen in the uric acid decomposition reaction.

Figure 5D:
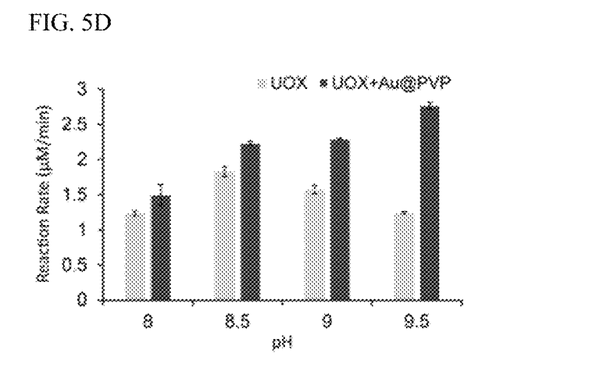

Referring to FIG. 5(D), it exhibits a faster uric acid decomposition rate in the case of UOX+Au@PVP than in the case of UOX alone, at pH range of 8.0 to 9.5, and particularly, UOX+Au@PVP has the highest uric acid decomposition rate at pH 9.5. At pH 8.5, it can confirm that UOX+Au@PVP showed an increase in uric acid decomposition ratio of about 20% or more compared to UOX. Also, at pH 8.5 or more, the decomposition rate of uric acid by UOX was gradually decreased as the pH increases, at the time of UOX alone.

However, when 5.0 µg/mL Au@PVP at pH 9.0~9.5 was added, the uric acid decomposition rate was increased by about 40% or more, and about 120% or more, respectively, compared with UOX alone.

Therefore, it can be seen that the higher the pH, the more the catalytic activity of Au@PVP increases.

Next, the rate which uric acid is decomposed was measured by varying the concentration of Au@PVP.

In the presence of 5 mM UOX, the degradation of uric acid by 6.25 µg/mL Au@PVP or 12.5 µg/mL Au@PVP was only 0.57% or 0.03% for 3 hours, respectively. It shows a result that it is difficult to generate a direct degradation of uric acid by polymer-coated gold nanoparticles.

Figure 6:
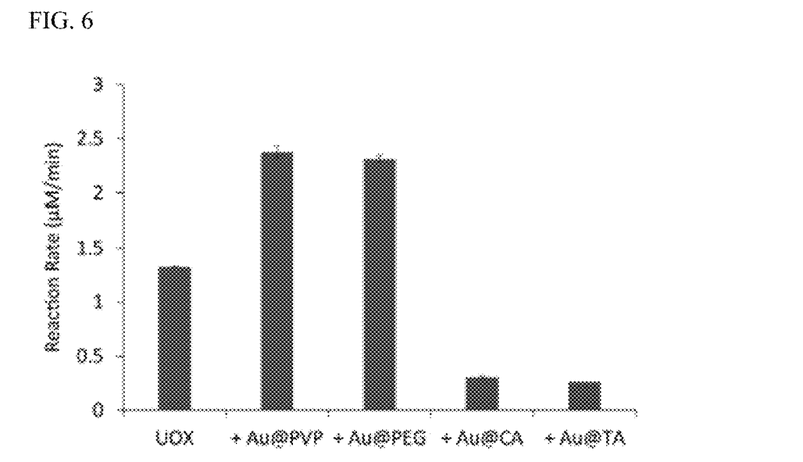
FIG. 6 is a graph showing a decomposition rate of uric acid according to the kind of polymer coated on the gold nanoparticles.

FIG. 6 is a graph showing the decomposition rate of uric acid according to the kind of polymer coated on gold nanoparticles. The addition of gold nanoparticles (AuNP) coated with PVP (Au@PVP) or PEG (Au@PEG) increased uric acid decomposition rates by about 73% or more than in the case of UOX alone.

As shown in FIG. 4, Au@CA and Au@TA had a faster decomposition rate of hydrogen peroxide, while the decomposition rate of uric acid was reduced by about 20% or more, compared to Au@PVP and Au@PEG.

The hexa-histidine tag (his-tag) of the protein has been reported to bind to the surface of gold nanoparticles via metal histidine coordination. When the stabilizer (polymer) is small and binds weakly to the surface of gold nanoparticles, the protein having the hexa-histidine tag is easily bound to the gold surface. In the present invention, Au@CA and Au@TA bind more easily to UOX than Au@PVP and Au@PEG, thereby affecting the structure of UOX and reducing the activity of UOX.

Figure 7:
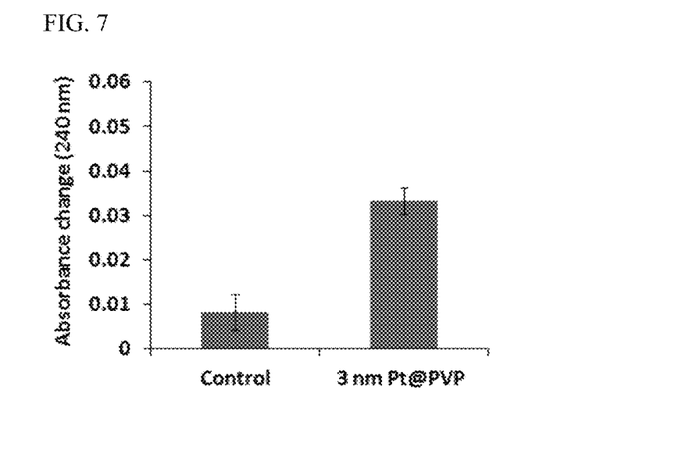
FIG. 7 is a graph showing a decomposition rate of uric acid according to Control and UOX+Pt@PVP in 20 mM borate buffer (pH 7.4).
Figure 8:
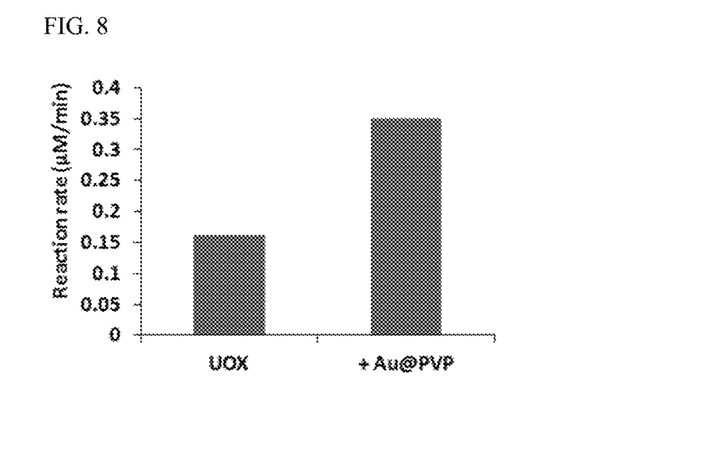
FIG. 8 is a graph showing the decomposition activity of hydrogen peroxide according to UOX alone and UOX+Au@PVP (average particle diameter 3 nm) in 20 mM borate buffer (pH 7.4).
Figure 9:
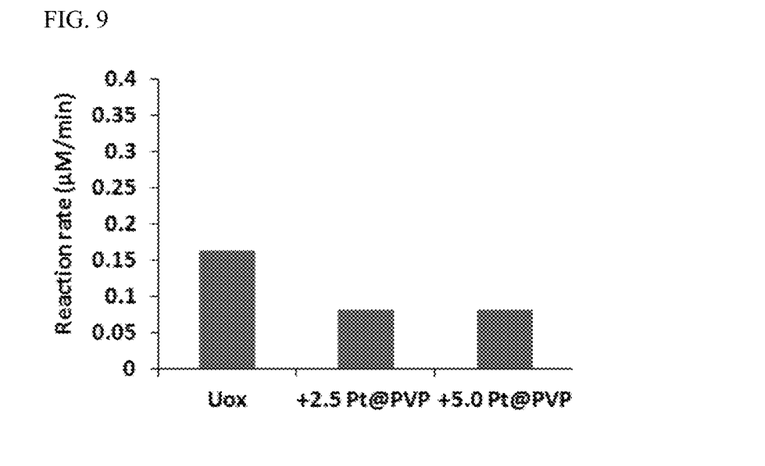
FIG. 9 is a graph showing a decomposition rate of 100 μM uric acid according to 5 mM UOX alone and 5 mM UOX+2.5, 5.0 μg/mL Pt@PVP in 20 mM borate buffer (pH 7.4).

FIGS. 7 to 9 are the graphs UOX activities comparing of UOX of PVN-coated gold nanoparticles and PVP-coated platinum nanoparticles. The control in FIG. 7 means an example in which only hydrogen peroxide is present without UOX enzyme, gold nanoparticles.

Referring to FIG. 8, in 20 mM borate buffer (pH 7.4), gold nanoparticles coated with polyvinylpyrrolidone (PVP) decompose hydrogen peroxide. In FIG. 8, it shows a result that the uric acid decomposition rate at the time of UOX+Au@PVP is 0.3 µM/min or more while it shows a result that the uric acid decomposition rate at the time of UOX+Pt@PVP is decreased to 0.1 µM/min or less, in FIG. 9.

That is, while Au@PVP increases the activity of UOX, Pt@PVP decreases the activity of UOX.

In this way, by mixing the gold nanoparticles formed with the polymer coating layer on UOX, the uric acid can be decomposed more effectively than when using UOX alone. In addition, by removing hydrogen peroxide with cytotoxicity and supplying oxygen to UOX while decomposing UOX, it can be seen that the average particle diameter of gold nanoparticles and the kinds of the stabilizer affects hydrogen peroxide decomposition rate and the uric acid decomposition rate.

While the embodiments of the present invention have been described with reference to the accompanying drawings, it will be understood that the present invention can be made in the different forms from each other, and is not limited to the above mentioned embodiments, and it can be implemented in the different specific form without changing the technical idea or the necessary feature of the present invention by those skilled in the art to which the present invention pertains. Therefore, the above-described embodiments are illustrative in all aspects and not restrictive.

What is claimed is:

1. A composition for uric acid decomposition, comprising urate oxidase (UOX), gold particles, and a buffer.

2. The composition for uric acid decomposition of claim 1, wherein gold nanoparticles have a polymer coating layer formed on a surface thereof,
    wherein the polymer comprises at least one of polyvinylpyrrolidone (PVP) and polyethylene glycol (PEG).

3. The composition for uric acid decomposition of claim 1, wherein the gold nanoparticles have an average particle diameter of 5 to 20 nm.

4. The composition for uric acid decomposition of claim 1, wherein the composition for uric acid decomposition comprises 0.5 to 5 µg/mL of gold nanoparticles.

5. The composition for uric acid decomposition of claim 1, wherein a concentration of the uricolytic enzyme is 1 to 20 nM.

6. The composition for uric acid decomposition of claim 1, wherein the buffer comprises a phosphate buffered saline (PBS), a tris buffer, a carbonate buffer, a borate buffer or a phosphate buffer.

7. The composition for uric acid decomposition of claim 6, wherein a pH of the buffer is 8.0 to 9.5.

8. The composition for uric acid decomposition of claim 6, wherein a concentration of the buffer is 5 to 30 mM.

* * * * *